(12) United States Patent
Robert et al.

(10) Patent No.: US 7,906,001 B2
(45) Date of Patent: Mar. 15, 2011

(54) METHOD FOR SEPARATING PROTEINS BY CAPILLARY ELECTROPHORESIS AND BUFFER COMPOSITIONS FOR CAPILLARY ELECTROPHORESIS

(75) Inventors: Frédéric Robert, Mennecy (FR); Denis Simonin, Evry (FR)

(73) Assignee: Sebia (FR)

( * ) Notice: Subject to any disclaimer, the term of this patent is extended or adjusted under 35 U.S.C. 154(b) by 1211 days.

(21) Appl. No.: 11/125,752

(22) Filed: May 10, 2005

(65) Prior Publication Data

US 2005/0274616 A1  Dec. 15, 2005

(30) Foreign Application Priority Data

May 10, 2004  (FR) ..................... 04 05039

(51) Int. Cl.
*G01N 27/26* (2006.01)
*G01N 27/447* (2006.01)
(52) U.S. Cl. ......... 204/451; 204/468; 204/601; 204/450; 252/62.2; 435/7.1; 436/517
(58) Field of Classification Search .................. 204/450, 204/451, 468, 601; 436/517; 435/7.1; 252/62.2
See application file for complete search history.

(56) References Cited

U.S. PATENT DOCUMENTS

| 4,654,132 | A | 3/1987 | Takagi et al. |
| 5,120,413 | A | 6/1992 | Sternberg et al. |
| RE36,011 | E | 12/1998 | Grushka et al. |
| 5,928,484 | A | 7/1999 | Bellon et al. |
| 5,964,999 | A * | 10/1999 | Guttman et al. ............... 204/455 |
| 6,193,891 | B1 * | 2/2001 | Kent et al. ..................... 210/645 |
| 2002/0162744 | A1 * | 11/2002 | Nouadje et al. ............... 204/451 |
| 2002/0195341 | A1 | 12/2002 | Robert |

FOREIGN PATENT DOCUMENTS

| EP | 0 518 475 A | 12/1992 |
| EP | 0 546 916 | 6/1993 |
| EP | 1 229 325 | 8/2002 |
| EP | 1 258 724 | 11/2002 |
| WO | WO-03/102225 | 12/2003 |

OTHER PUBLICATIONS

Kris-Etherto et al. (Journal of Lipid Research vol. 21, 1980), 435-442.*
Bossuyt et al., "Automated Serum Protein Electrophoresis by Capillarys®" 41 Clin. Chem. Lab. Med. (2003) 704-710.

(Continued)

*Primary Examiner* — Alexa D Neckel
*Assistant Examiner* — Jennifer Dieterle
(74) *Attorney, Agent, or Firm* — Lerner, David, Littenberg, Krumholz & Mentlik, LLP

(57) ABSTRACT

The invention concerns a free solution capillary electrophoresis method at alkaline pH for the analysis of samples comprising protein constituents including a lipoprotein constituent or constituents, characterized in that it comprises at least one step in which the sample is introduced into a capillary tube containing an analysis buffer, said analysis buffer further comprising at least one anionic surfactant type additive that is capable of hydrophobic interaction with the lipoprotein constituent(s) and of modifying the electrophoretic mobility. The invention also concerns a composition for capillary electrophoresis and a kit for analyzing protein constituents.

30 Claims, 3 Drawing Sheets

3A

3B

3C

3D

OTHER PUBLICATIONS

Tadey & Purdy, "Characterization of plasma apolipoproteins by capillary electrophoresis," 583 J. Chromatography (1992) 111-115.

Stocks & Miller, "Analysis of apolipoproteins and lipoproteins by capillary electrophoresis," 20 Electrophoresis (1999) 2118-23.

Tadey & Purdy, "Effect of detergents on the electophoretic behaviour of plasma apolipoproteins in capillary electrophoresis," 652 J. Chromatography (1993) 131-38.

* cited by examiner

3A

3B

3C

3D

METHOD FOR SEPARATING PROTEINS BY CAPILLARY ELECTROPHORESIS AND BUFFER COMPOSITIONS FOR CAPILLARY ELECTROPHORESIS

The present invention relates to a method for separating proteins and peptides by capillary electrophoresis and to buffer compositions comprising an additive for use in said separation, in the presence of lipoproteins in the sample.

Analyzing the amount of proteins in biological liquids such as serum for analytical and particularly for diagnostic purposes is known, usually for the separation of proteins by electrophoresis, both using gel electrophoresis and capillary electrophoresis. One of the advantages of capillary electrophoresis is that only very small quantities of biological liquids to be analyzed are required. Further, separation using this technique can be very rapid provided that high voltages can be used without heating the sample up too much during separation.

To separate serum proteins, capillary electrophoresis is conventionally carried out with alkaline buffers. Usually, the protein profiles obtained comprise five or six fractions which correspond to the protein constituents, namely the albumin fraction, the $\alpha_1$- and $\alpha_2$-fractions, the $\beta$-globulin fractions or the $\beta_1$- and $\beta_2$-fractions, and the $\gamma$-globulin fraction. Each of these fractions comprises one or more serum protein(s).

Such separations can be carried out using capillary electrophoresis and analytical buffers, techniques such as those described in U.S. Pat. No. Re 36 011, and in European patents EP-A-0 518 475, EP-A-1 229 325 or EP-A-1 258 724.

However, separating serum proteins can sometimes prove unsatisfactory.

In fact, the term "protein constituent" means here not only the protein constituents, namely the $\alpha_1$-; $\alpha_2$-; $\beta$- or $\beta_1$-; and $\beta_2$-; and $\gamma$-globulin fractions, but also the lipoprotein constituents, mainly $\alpha$-lipoproteins, $\beta$-lipoproteins and pre-$\beta$-lipoproteins, also known as HDL, LDL and VLDL for "high density lipoprotein", "low density lipoprotein" and "very low density lipoprotein". The profiles are sometimes inaccurate, primarily because of those lipoproteins, principally $\beta$-lipoprotein and pre-$\beta$-lipoprotein, which appear in the zone of the profile corresponding to the $\alpha_1$- and $\alpha_2$-globulins and $\beta_1$-globulin.

The Applicant has now shown that using an anionic surfactant as an additive to the analysis buffer can result in improved separation, and in particular a purer profile in the $\alpha_1$- and $\alpha_2$- and $\beta_1$-globulin zone of the electrophoretic profile. Said additives are selected from anionic surfactants that are capable of hydrophobic interactions with one or more lipoprotein constituents, and in particular the hydrophobic residues of lipoproteins. They may supply the lipoprotein constituent or constituents with one or more negative charges. They may modify, and in particular reduce, the electrophoretic mobility with respect to that of other protein constituents.

At low concentrations of said additive as used according to the present invention, which concentrations are low with regard to the concentrations used for the additives in other applications, the profiles obtained in capillary electrophoresis could present as very pure peaks, exempt from shoulders, especially concerning the $\alpha_1$ and $\alpha_2$ fractions, as it is apparent from the examples. This is a large interest for the exploitation of profiles of hyperlipemic serum, especially, and presents equally a certain interest for the analysis of normolipemic samples.

Thus, the invention concerns a free solution capillary electrophoresis method at alkaline pH for the analysis of samples comprising protein constituents including a lipoprotein constituent or constituents, in which the sample is introduced into a capillary tube containing an analysis buffer, said analysis buffer further comprising at least one anionic surfactant type additive that is capable of hydrophobic interaction with one (or more) lipoprotein constituent(s). Said additive is capable of supplying one or more negative charges to said lipoprotein constituent or constituents and to thereby modify the electrophoretic mobility with respect to that of other non-lipidic protein constituents.

Said step is generally followed by separating the protein constituents by migration and detecting the constituents.

The invention also concerns a method for separating, by electrophoresis, the protein constituents of samples comprising at least albumin and $\alpha_1$-, $\alpha_2$- and $\beta_1$-globulin fractions, as well as lipoproteins, in an analysis buffer, in which the analysis buffer further comprises at least one anionic surfactant type additive that is capable of hydrophobic interaction with the lipoproteins.

The present invention also concerns a method for electrophoretic separation by free solution capillary electrophoresis at alkaline pH of protein constituents of a liquid sample comprising lipoproteins, in which method the sample comprising said constituents is passed through a capillary containing an analysis buffer further comprising an additive that is capable of specifically interacting with the lipoproteins; the additive may be an anionic surfactant comprising a hydrophobic portion such as a $C_{10}$ to $C_{20}$ alkyl chain, and an anionic portion supplying a strong negative charge at a pH of more than 9.

The anionic surfactant type additive is used at low concentrations in the buffer so that the interaction with the albumin or other non-lipidic protein constituents remains weak and particularly centered on the lipoproteins, herein termed "lipoprotein-specific". For such a lipoprotein-specific interaction, it is preferable to use the anionic type surfactant additive at low concentrations. For each anionic surfactant, said concentrations depend partly on its affinity for lipoproteins and partly on its affinity for albumin or for other non-lipidic protein constituents. The optimum concentration is thus different for each surfactant. It may be of the order of less than 1 mM in the buffer, for example of the order of 0.001 mM to 0.2 mM, preferably more than 0.01 mM and less than 0.1 mM, for example in the range 0.01 mM to 0.09 mM, for example.

The Applicants have verified, especially for SDS, that a concentration of about 0.05 mM does not involve a sufficient shift of lipoproteic constituents and that at concentrations superior to 0.2 mM the profiles are deformed (diminution of the $\beta_2$ fraction and deformation of the $\alpha_1$ fraction at 0.25 mM, and at a concentration of 0.5 mM a totally deformed profile is even obtained).

Thus, compounds used as an additive for the capillary electrophoresis analysis buffer of the invention that are capable of a specific hydrophobic interaction with lipoproteins may be anionic surfactants such as those used in MECC (micellar electrokinetic capillary chromatography), but at a concentration that is substantially lower than the critical micellar concentration. In the present invention, said compounds are used in free solution CE as indicated above, and the lipoproteins are supplied with negative charges by hydrophobic interaction between the hydrophobic residues of said lipoproteins and the hydrophobic portion of said compounds, resulting in slower migration of said lipoproteins with respect to that of other proteins. One consequence is the improved separation of $\alpha_1$, $\alpha_2$ and $\beta_1$ fractions, the lipoproteins migrating beyond the zones to which they usually migrate, i.e. the $\alpha_1$, $\alpha_2$ and $\beta_1$ zones. They are also used at a concentration that is lower than the concentrations described in EP-A-1 229 325.

Further, the invention concerns electrolyte compositions for capillary electrophoresis comprising, in an acceptable support, at least one buffer and an anionic surfactant type additive as defined above, capable of causing lipoproteins to migrate beyond the zones to which they usually migrate, in particular beyond the zones for fractions $\alpha_1$, $\alpha_2$ and $\beta_1$ fractions.

As will be shown in the examples, the use of the additives of the invention allows greatly improved separation of $\alpha_1$, $\alpha_2$ and $\beta_1$ fractions by displacement of the lipoproteins beyond their usual zone. It can thus improve the speed and accuracy of the quantitative analysis of serum proteins compared with analyses carried out with the usual buffers. The additives are of particular advantage for the analysis of biological samples which are rich in $\beta$-lipoprotein and pre-$\beta$-lipoprotein.

Finally, the invention concerns kits for analyzing the protein constituents of a biological sample, comprising at least one analysis buffer and an anionic surfactant type additive capable of causing lipoproteins to migrate beyond zones to which they normally migrate, in particular beyond the zones for the $\alpha_1$, $\alpha_2$ and $\beta_1$ fractions and/or comprising a hydrophobic portion, such as a $C_{10}$ to $C_{20}$ alkyl chain, and an anionic portion supplying a strong negative charge at a pH of more than 9 and/or one or more capillary rinsing solution(s) and/or dilution segments and/or one or more diluents for the sample to be analyzed. In this kit, the buffer and the additive(s) and diluent(s) may be stored separately for extemporaneous mixing, or they may be stored as a mixture. Said kit optionally comprises instructions for carrying out the analysis.

Further characteristics and advantages of the invention will become apparent from the following detailed description and examples and from the accompanying figures.

Figure 1:
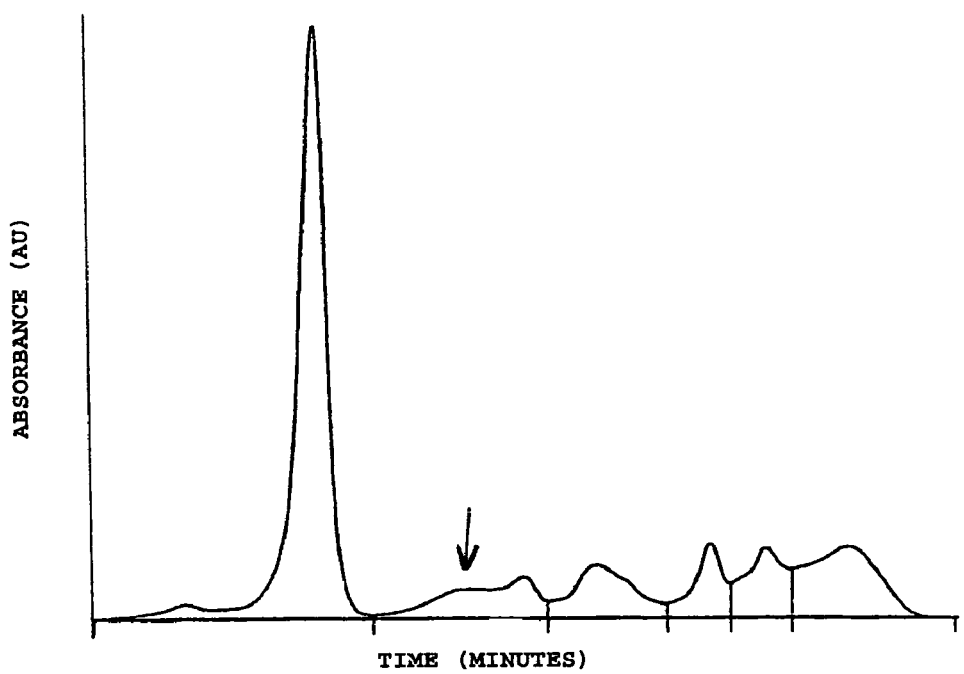
FIG. 1 shows an electropherogram of a human serum analyzed by capillary electrophoresis using a buffer in accordance with EP-A-1 229 325.

The conditions for carrying out capillary electrophoresis (CE) are known in the art. They may usually comprise rinsing the capillaries with a rinsing solution, rinsing with analysis buffer, optionally diluting the sample one or more times, injecting the sample, migration and detection. Said steps may be carried out using automatic machines.

The conditions for carrying out capillary electrophoresis are, for example, conditions suitable for use with the Capillarys (SEBIA) automatic machine.

Compounds comprising an anionic pole supplying a strong negative charge at an alkaline pH and a hydrophobic portion may be used as additives for the buffer in accordance with the invention and which are capable of interacting with the hydrophobic portion of lipoproteins.

The hydrophobic alkyl chain may be composed of at least one $C_{10}$ to $C_{24}$ alkyl chain, which may or may not be branched, comprising at least one linear portion of about 10 carbon atoms, in particular 10 to 20 carbon atoms. As will be readily understood by the skilled person, said hydrophobic portion may comprise residues or functions which do not essentially modify its hydrophobic nature.

The anionic pole may be constituted by one or more groups or chemical functions from the following list: sulphonates, carboxylates, sulphates and phosphates.

In particular, the following can be cited: anionic surfactants such as $C_{10}$-$C_{24}$ alkyl mono-, di- or tri-sulphates, $C_{10}$-$C_{24}$ alkyl mono-, di- or tri-sulphonates, $C_{10}$-$C_{24}$ alkyl mono-, di- or tri-carboxylates, $C_{10}$-$C_{24}$ alkyl mono-, di- or tri-phosphates and $C_{10}$-$C_{24}$ alkylcarboxy-sulphonates, -sulphates and -phosphates, in particular $C_{10}$ to $C_{24}$ alkylsulphates.

The above di- or tri-carboxylates, di- or tri-sulphonates, di- or tri-sulphates and di- or tri-phosphates and carboxy-sulphonates, -sulphates and -phosphates are thus combinations of one or more carboxylate, sulphate, sulphonate or phosphate functions on alkyl chains containing 10 to 24 carbon atoms.

Preferred anionic surfactants from those cited above are $C_{10}$-$C_{24}$ monoalkylsulphates, particularly $C_{10}$ to $C_{20}$ alkylsulphates, and of these, $C_{10}$ to $C_{16}$ alkylsulphates.

Said compounds are known per se and are available commercially. They may be in the acidic form or in the form of salts, in particular alkali metal salts.

The dodecylsulphate is particularly preferred, more precisely sodium dodecylsulphate (SDS).

In the above denominations, the alkyl radicals are preferably linear.

The anionic surfactant type additives defined above may also be used as a mixture.

Further, the anionic surfactant type additives may advantageously be used in the presence of other additives known to interact with albumin, by improving the distance between $\alpha_1$-globulin and albumin as described in EP-A-1 229 325.

Preferred additives that are cited in EP-A-1 229 325 for their interaction with albumin are $C_6$ to $C_{10}$ alkylsulphonates, and of these $C_6$ to $C_{10}$ alkylsulphonates, the octanesulphonate is particularly preferred, as it substantially improves the clarity of the profiles due to the separation between $\alpha_1$-globulin and albumin.

The term "sample in accordance with the invention" means the biological sample to be analyzed, previously diluted with a suitable diluting solution or an analysis buffer, for example, or pure.

Any liquid biological sample from healthy or ailing patients can be analyzed. Thus, human liquid biological samples may be normal or abnormal serum, as well as haemolyzed blood, plasma, urine or cerebro-spinal fluid. In addition to human biological samples, samples of animal origin may also be analyzed. The samples may also be synthetic proteins, and the method of the invention may then be targeted at production control, for example.

The additives of the invention are of particular use for the analysis of serum, and the separation of serum proteins in human samples.

In the serum samples, the serum proteins to be separated are albumin and the $\alpha_1$-; $\alpha_2$-; $\beta$ (or $\beta_1$- and $\beta_2$-); and $\gamma$-globulin fractions, and $\alpha$-lipoproteins, $\beta$-lipoproteins and pre-$\beta$-lipoproteins, in particular $\beta$-lipoproteins and pre-$\beta$-lipoproteins. Said denominations may include protein constituents from all sub-types of said classes.

The analysis buffer may be any known analysis buffer suitable for the desired separation and for electrophoresis in general, and capillary electrophoresis in particular. Examples which may be cited are borate, phosphate and carbonate buffers, buffers based on amino acids and biological buffers. In particular, the Capillarys B1B2+buffer (SEBIA) may be used.

Biological buffers which may be cited are buffers known as Bis-TRIS (2-bis[2-hydroxyethyl]amino-2-hydroxymethyl-1,3-propanediol), ADA (N-[2-acetamido]-2-iminodiacetic acid), ACES (2-[2-acetamino]-2-aminoethanesulphonic acid), PIPES (1,4-piperazinediethanesulphonic acid), MOPSO (3-[N-morpholino]-2-hydroxypropanesulphonic acid), Bis-TRIS PROPANE (1,3-bis[tris(hydroxymethyl)methylaminopropane]), BES (N,N-bis[2-hydroxyethyl]-2-aminoethanesulphonic acid), MOPS (3-[N-morpholino]propanesulphonic acid), TES (2-[2-hydroxy-1,1-bis(hydroxymethyl)ethylamino]ethanesulphonic acid), HEPES (N-[2-hydroxyethyl]piperazine-N'-(2-ethanesulphonic) acid), DIPSO (3-N,N-bis[2-hydroxyethyl]amino-2-hydroxypropanesulphonic) acid), MOBS (4-N-morpholinobutanesulphonic acid), TAPSO (3[N-tris-hydroxymethyl-methylamino]-2-hydroxypropanesulphonic acid), TRIS (2-amino-2-[hydroxymethyl]-1,3-propanediol), HEPPSO (N-[2-hydroxyethyl]piperazine-N'-[2-hydroxypropanesulphonic] acid), POPSO (piperazine-N,N'-bis[2-hydroxypropanesulphonic] acid), TEA (triethanolamine), EPPS (N-[2-hydroxyethyl]-piperazine-N'-[3-propanesulphonic] acid), TRICINE (N-tris[hydroxymethyl]methylglycine), GLY-GLY (diglycine), BICINE (N,N-bis[2-hydroxyethyl]-glycine), HEPBS (N-[2-hydroxyethyl]piperazine-N'-[4-butanesulphonic] acid), TAPS (N-tris[hydroxymethyl]methyl-3-aminopropanesulphonic] acid), AMPD (2-amino-2-methyl-1,3-propanediol), TABS (N-tris[hydroxymethyl]methyl-4-aminobutanesulphonic acid), AMPSO (3-[(1,1-dimethyl-2-hydroxyethyl)amino]-2-hydroxypropanesulphonic acid), CHES (2-(N-cyclohexylamino)ethanesulphonic acid), CAPSO (3-[cyclohexylamino]-2-hydroxy-1-propanesulphonic acid), AMP (2-amino-2-methyl-1-propanol), CAPS (3-cyclohexylamino-1-propanesulphonic acid) or CABS (4-[cyclohexylamino]-1-butanesulphonic acid), preferably AMPD, TABS, AMPSO, CHES, CAPSO, AMP, CAPS or CABS.

In alkaline pH capillary electrophoresis, the pH of the analysis buffer is in the range 8 to 12, preferably in the range 9 to 11, and more particularly preferably at a value of about 10.

The analysis buffers of the invention may also comprise at least one compound which modifies the pH. Examples of pH modifiers which may be used are compounds selected from lithium hydroxide, sodium hydroxide, potassium hydroxide, rubidium hydroxide, caesium hydroxide, francium hydroxide, and mono-, di-, tri- or tetra-alkyl ammonium hydroxide containing 1 to 8 carbon atoms in the alkyl portion.

According to the invention, the analysis buffers are used under the usual conditions and in the usual concentrations, namely of the order of 10 to 500 mM, preferably 20 to 400 mM.

The additives of the invention are used in the concentrations defined above, which are low compared with the concentrations described in EP-A-1 229 325 in the context of their interaction with albumin. In general, it is of the order of 0.001 to 0.2 mM, preferably 0.01 to 0.09 mM, and in the case of SDS, it is less than that which would cause too great an interaction with albumin or other non lipidic protein constituents, namely which would perturb the profile too greatly.

More specific additives known to interact with albumin are used in concentrations of 0.1 mM to 500 mM without, however, exceeding their critical micellar concentration in the analysis buffer. This critical micellar concentration value is valid for additives which are surfactants.

When octanesulphonate is used, its concentration in the buffer is of the order of 1 to 10 mM, preferably 2.5 to 5 mM. Its use in the presence of SDS may counteract the effect of SDS on peak displacement in particular in the albumin zone.

Further, the buffer may comprise one or more additives which can increase the ionic strength.

Examples of said additives for the buffer which may increase the ionic strength of the electrolyte which may be cited are compounds selected from chlorides, sulphates, sulphonates, carbonates, carboxylates, fluorides and phosphates of alkali metals and their mixtures. Of these, chlorides, sulphates or sulphonates of alkali metals and their mixtures are preferred.

More preferably, the sulphate is used. Preferably, sodium, lithium or potassium salts are selected. Of the additives cited above, sodium and/or lithium sulphate is preferred.

The buffer compositions of the invention are prepared in the manner usual for analysis buffer compositions, namely by adding the constituents in the liquid form or in the solid form to be diluted, to an acceptable support. The support is usually water, which may be distilled or demineralized.

The materials used for the capillaries are those which are normal in capillary electrophoresis. Thus, fused silica capillaries may be used. Their internal diameter may be from 5 to 2000 µm. Preferably, capillaries with an internal diameter of less than 200 µm may be used, more preferably less than 100 µm. Preferably, capillaries with an untreated inner surface are used. The skilled person will be able to adapt the nature of the capillary and its size to the analysis requirements.

EXAMPLES

Methods and Apparatus

A) Capillary Electrophoresis

Capillary electrophoresis of clinical samples was carried out using a CE apparatus equipped with a fused silicon capillary having an internal diameter of 25 microns. Detection was carried out at 200 nm. The samples were placed in the sample tray of the Capillarys apparatus (SEBIA) and automatically injected by hydrodynamic injection. Sample separation was carried out in less than 5 minutes by applying an electric field of about 400 V/cm. The capillary was rinsed prior to each analysis using 0.25 M sodium hydroxide then the analysis buffer.

Analysis Buffers:

The chemicals used were of analytical grade.

The 150 mM borate buffer was prepared by dissolving 9.3 g of boric acid (molar mass: 61.83 g/mol) in 1 litre of demineralized water, along with 5.1 g of sodium hydroxide (molar mass: 40.0 g/mol). The final concentration was 150 mM and the pH was 10.0.

B) Clinical Samples

For CE, human serum was diluted to one fifth in the analysis buffer.

Example 1 (Comparative)

A borate analysis buffer was prepared as described above.

Electrophoresis was carried out using the above method on hyperlipemic human serum (triglycerides: 5.73 g/l).

As can be seen in FIG. 1, the electropherogram obtained has, from left to right, six successive peaks attributed respectively to the albumin and to the $\alpha_1$, $\alpha_2$, $\beta_1$, $\beta_2$ and $\gamma$-globulin fractions.

| Fraction | % |
|---|---|
| Albumin | 52.3 |
| Alpha 1 | 9.7 |
| Alpha 2 | 9.6 |
| Beta 1 | 6.4 |
| Beta 2 | 7.8 |
| Gamma | 14.2 |

Example 2

SDS was added in a concentration of 0.07 mM to the analysis buffer of Example 1.

Electrophoresis was carried out as described in Example 1.

Figure 2:
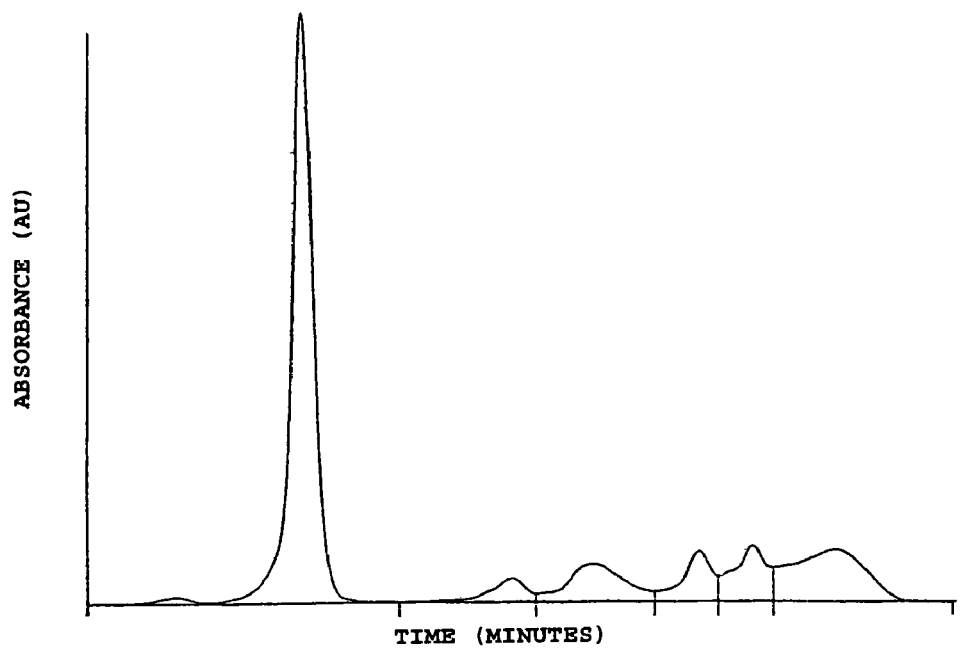
FIG. 2 shows an electropherogram of the same serum analyzed by capillary electrophoresis using the same buffer, further comprising, however, an anionic surfactant additive of the invention.

As can be seen in FIG. 2, the electropherogram obtained has, from left to right, six successive peaks attributed respectively to the albumin and to the $\alpha_1$, $\alpha_2$, $\beta_1$, $\beta_2$ and $\gamma$-globulin fractions. Comparison with Example 1 shows that the separation between the two fractions was substantially improved. The peak marked by an arrow as a shoulder on the alpha-1 peak (corresponding to the pre β-lipoproteins) was eliminated from the profile.

| Fraction | % |
|---|---|
| Albumin | 57.7 |
| Alpha 1 | 3.9 |
| Alpha 2 | 9.1 |
| Beta 1 | 6.2 |
| Beta 2 | 7.6 |
| Gamma | 15.5 |

Example 3

Electrophoresis of normolipemic human serum (triglycerides 1.10 g/l) was undertaken in the same manner as the preceding examples with the addition of SDS to the buffer at 0.00; 0.05; 0.07 and 0.25 mM concentration.

These electropherograms that were obtained present from the left to the right 6 successive peaks attributed to the albumin fraction and to the $\alpha_1$-, $\alpha_2$-, $\beta_1$-, $\beta_2$- and $\gamma$-globulin fractions. The table below represents the obtained results.

Figure 3:
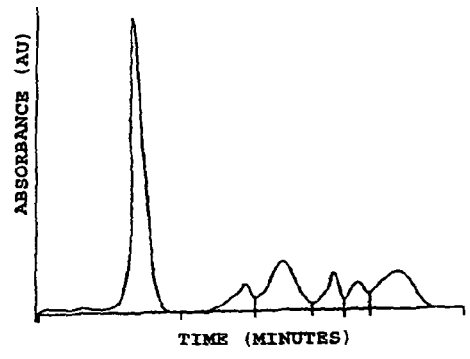
FIGS. 3A, 3B, 3C and 3D represent electrophoregrams of a same normolipemic serum by EC and using the same buffer to which is added 0; 0.05; 0.07 and 0.25 mM SDS, respectively.
Figure 3:
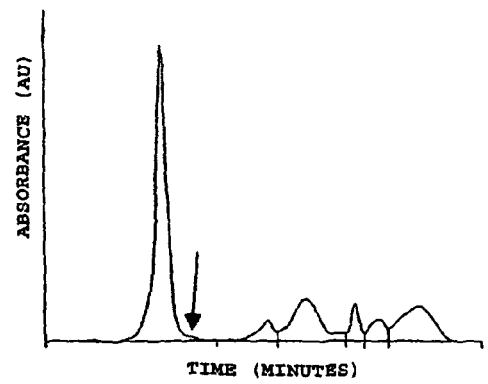
Figure 3:
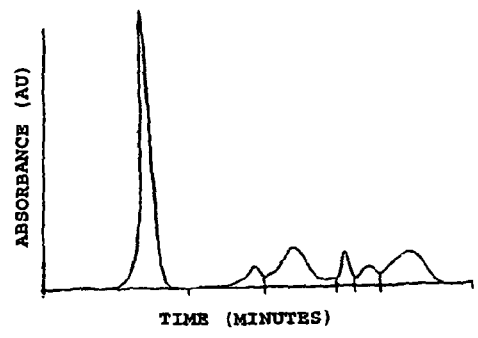
Figure 3:
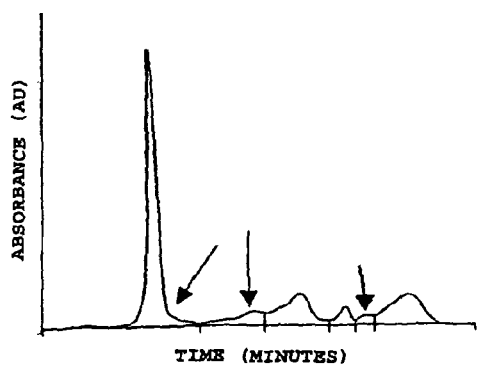

| | % SDS concentration (mM) | | | |
|---|---|---|---|---|
| | 0.00 | 0.05 | 0.07 | 0.25 |
| FRACTION | FIG. 3A | FIG. 3B | FIG. 3C | FIG. 3D |
| Albumin | 50.4 | 50.5 | 49.1 | 52.4 |
| $\alpha_1$ | 6.5 | 5.2 | 6.0 | 7.3 |
| $\alpha_2$ | 16.2 | 17.9 | 18.3 | 16.5 |
| $\beta_1$ | 6.2 | 5.0 | 4.9 | 4.1 |
| $\beta_2$ | 5.4 | 4.9 | 4.8 | 2.3 |
| $\gamma$ | 15.3 | 16.5 | 16.9 | 17.4 |
| | Light lipemic interference on albumin peak | No interference | | Deformation of $\alpha_1$ fraction; light shoulder on albumin peak; diminution of $\beta_2$ fraction |

Example 4

Using the same process as example 3 with hyperlipemic human serum (triglycerides 5.63 g/l). These electropherograms that were obtained present from the left to the right 6 successive peaks attributed to the albumin fraction and to the $\alpha_1$-, $\alpha_2$-, $\beta_1$-, $\beta_2$- and $\gamma$-globulin fractions. The table below represents the obtained results.

Figure 4:
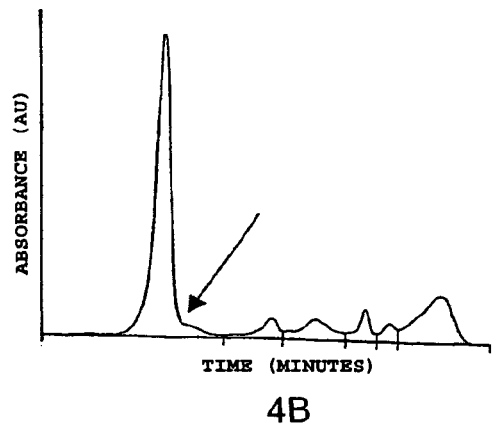
FIGS. 4A, 4B, 4C and 4D represent the electrophoregrams of a same hyperlipemic serum by EC and using the same buffer to which is added 0; 0.05; 0.07 and 0.25 mM SDS respectively.
Figure 4:
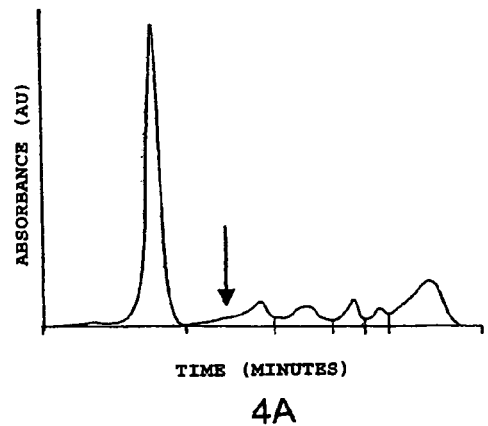
Figure 4:
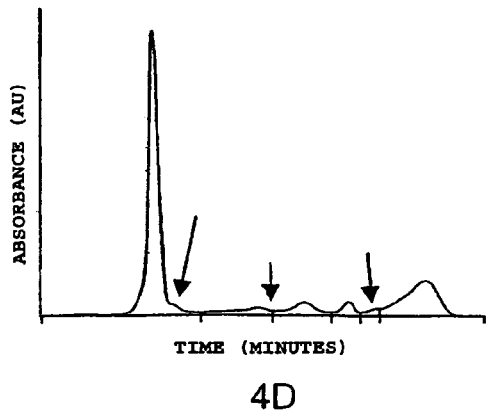
Figure 4:
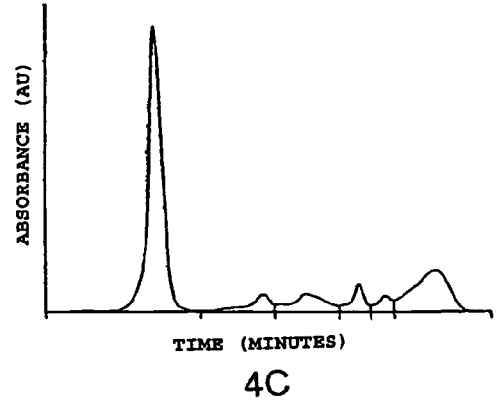

| | % SDS concentration (mM) | | | |
|---|---|---|---|---|
| | 0.00 | 0.05 | 0.07 | 0.25 |
| FRACTION | FIG. 4A | FIG. 4B | FIG. 4C | FIG. 4D |
| Albumin | 54.7 | 59.1 | 57.2 | 58.7 |
| $\alpha_1$ | 9.7 | 4.9 | 5.6 | 5.9 |
| $\alpha_2$ | 7.9 | 8.3 | 8.6 | 7.2 |
| $\beta_1$ | 5.0 | 5.0 | 4.9 | 3.7 |
| $\beta_2$ | 3.4 | 3.2 | 3.4 | 1.8 |
| $\gamma$ | 19.3 | 19.5 | 20.3 | 22.7 |
| | Lipemic interference; shoulder on $\alpha_1$ | Shoulder on albumin peak | No interference | Interference with albumin peak; deformation of $\alpha_1$ fraction; diminution of $\beta_2$ fraction. |

The invention claimed is:

1. A method for separating by free solution capillary electrophoresis, at alkaline pH protein constituents selected from the group consisting of albumin and $\alpha_1$-, $\alpha_2$-, β- (or $\beta_1$- and $\beta_2$-) and γ-globulin fractions from lipoprotein constituents in a sample comprising:
    (a) introducing a sample into a capillary tube containing an analysis buffer, said analysis buffer comprising at least one anionic surfactant additive that hydrophobically interacts with said lipoprotein constituents and modifies the electrophoretic mobility with respect to said protein constituents, wherein said at least one anionic surfactant additive in said analysis buffer has a concentration in the range of 0.001 mM to less than 0.1 mM;
    (b) passing said sample through said capillary tube; and
    (c) separating said protein constituents and said lipoprotein constituents by electrophoresis.

2. The method according to claim 1, further comprising the step of detecting said protein constituents and said lipoprotein constituents.

3. The method according to claim 1, wherein the lipoprotein constituent(s) are selected from the group consisting of α-lipoprotein, β-lipoprotein and pre-β-lipoprotein.

4. The method according to claim 1, wherein said at least one anionic surfactant additive is sodium dodecylsulphate.

5. The method according to claim 1, wherein the concentration of said at least one anionic surfactant additive in said analysis buffer is in the range 0.01 mM to 0.09 mM.

6. The method according to claim 1, wherein said analysis buffer further comprises an octanesulphonate additive in a concentration in said analysis buffer in the range of 1 mM to 10 mM.

7. The method according to claim 1, wherein said analysis buffer has an alkaline pH in the range of 9 to 11.

8. The method according to claim 1, wherein said capillary tube is formed from fused silica.

9. The method according to claim 1, wherein said analysis buffer further comprises sodium sulphate or lithium sulphate.

10. The method according to claim 1, wherein said sample is a biological sample.

11. The method according to claim 10, wherein said sample is a sample of serum, hemolyzed blood, plasma, urine or cerebrospinal fluid.

12. The method according to claim 11, wherein said sample of serum is hyperlipemic serum.

13. The method according to claim 1, wherein said at least one anionic surfactant additive comprises an anionic pole at a pH of more than 9 and a hydrophobic portion.

14. The method according to claim 13, wherein said at least one anionic surfactant additive hydrophobic portion comprises at least one $C_{10}$ to $C_{24}$ alkyl chain, which may or may not be branched and a linear portion containing at least 10 carbon atoms, and said at least one anionic surfactant additive anionic pole comprises one or more groups selected from sulphonates, carboxylates, sulphates and phosphates.

15. The method according to claim 1, wherein said at least one anionic surfactant additive is selected from the group consisting of $C_{10}$-$C_{24}$ alkyl mono-, di- or tri-sulphates, $C_{10}$-$C_{24}$ alkyl mono-, di- or tri-sulphonates, $C_{10}$-$C_{24}$ alkyl mono-, di- or tri-carboxylates, $C_{10}$-$C_{24}$ alkyl mono-, di- or tri-phosphates and $C_{10}$-$C_{24}$ alkylcarboxy-sulphonates, sulphates and -phosphates.

16. The method according to claim 15, wherein said at least one anionic surfactant additive is a $C_{10}$ to $C_{20}$ alkylsulphate.

17. The method according to claim 1, wherein the concentration of said at least one anionic surfactant additive in said analysis buffer is of the order of 0.07 mM.

18. The method according to claim 17 wherein said anionic surfactant additive is sodium dodecylsulphate.

19. The method according to claim 1, wherein said analysis buffer further comprises at least one pH modifier.

20. The method according to claim 19, wherein said pH modifier is selected from the group consisting of lithium hydroxide, sodium hydroxide, potassium hydroxide, rubidium hydroxide, caesium hydroxide, francium hydroxide, and mono-, di- tri- or tetra-alkyl ammonium hydroxide containing 1 to 8 carbon atoms in the alkyl portion.

21. An electrolyte composition for capillary electrophoresis, comprising at least one buffer comprising at least one anionic surfactant additive that hydrophobically interacts with lipoproteins causing said lipoproteins to migrate beyond the zones to which they usually migrate for the $\alpha_1$, $\beta_2$ and $\beta_1$ fractions, the concentration of said at least one anionic surfactant additive in the buffer being in the range of 0.001 mM to less than 0.1 mM.

22. The electrolyte composition of claim 21 wherein the concentration of said at least one anionic surfactant additive in the buffer is in the range of 0.01 mM to 0.09 mM.

23. The electrolyte composition of claim 21, wherein said at least one anionic surfactant additive comprises a hydrophobic portion composed of at least one $C_{10}$ to $C_{24}$ alkyl chain, which may or may not be branched, comprising at least one linear chain containing 10 carbon atoms, and an anionic pole constituted by one or more groups selected from sulphonates, carboxylates, sulphates and phosphates.

24. The electrolyte composition of claim 23, characterized in that said at least one anionic surfactant additive is selected from the group consisting of $C_{10}$-$C_{24}$ alkyl mono-, di- or tri-sulphates, $C_{10}$-$C_{24}$ alkyl mono-, di- or tri-sulphonates, $C_{10}$-$C_{24}$ alkyl mono-, di- or tri-carboxylates, $C_{10}$-$C_{24}$ alkyl mono-, di- or tri-phosphates and $C_{10}$-$C_{24}$ alkylcarboxy mono-, di- or tri-sulphonates, sulphates and phosphates.

25. The electrolyte composition of claim 23, wherein said at least one anionic surfactant additive is selected from the group consisting of $C_{10}$ to $C_{24}$ alkylsulphate anionic surfactants and mixtures thereof.

26. The electrolyte composition of claim 23, wherein said at least one anionic surfactant additive is sodium dodecylsulphate.

27. The electrolyte composition of claim 26 wherein the concentration of sodium dodecylsulphate is of the order of 0.07 mM.

28. A kit for analyzing protein constituents in a biological sample, comprising at least one analysis buffer and an anionic surfactant additive which causes lipoproteins to migrate beyond the zones to which they usually migrate, wherein said zones are for the $\alpha_1$, $\alpha_2$ and $\beta_1$ fractions and comprises a hydrophobic portion such as a $C_{10}$ to $C_{20}$ alkyl chain and an anionic portion supplying a strong negative charge at a pH of more than 9; and/or a solution or solutions for rinsing capillaries and/or one or more suitable diluents and/or dilution segments, the concentration of said anionic surfactant additive in the analysis buffer being in the range of 0.001 mM to less than 0.1 mM.

29. A method for separating by free solution capillary electrophoresis, at alkaline pH, protein constituents selected from the group consisting of albumin and the $\alpha_1$-, the $\alpha_2$-, the $\beta$- (or $\beta_1$- and $\beta_2$-) and the $\gamma$-globulin fractions from lipoprotein constituents in a sample comprising:

(a) introducing a sample into a capillary tube containing an analysis buffer, wherein said analysis buffer comprises at least one anionic surfactant additive that hydrophobically interacts with said lipoprotein constituents and modifies the electrophoretic mobility with respect to said protein constituents, wherein said at least one anionic surfactant additive in said analysis buffer has a concentration in the range of 0.001 mM to less than 0.1 mM; and said at least one anionic surfactant additive in said analysis buffer causes said lipoprotein constituents to migrate beyond the zones to which they usually migrate for the $\alpha_1$, $\alpha_2$ and $\beta_1$ fractions, (b) passing said sample through said capillary tube; and (c) separating said protein constituents and said lipoprotein constituents by electrophoresis.

30. A method for separating by free solution capillary electrophoresis, at alkaline pH, protein constituents selected from the group consisting of albumin and the $\alpha_1$-, the $\alpha_2$-, the $\beta$- (or $\beta_1$- and $\beta_2$-) and the $\gamma$-globulin fractions from lipoprotein constituents in a sample comprising:

(a) introducing a sample into a capillary tube containing an analysis buffer, wherein said analysis buffer comprises at least one anionic surfactant additive that hydrophobically interacts with said lipoprotein constituents and modifies the electrophoretic mobility with respect to said protein constituents, wherein said at least one anionic surfactant additive in said analysis buffer has a concentration in the range of 0.001 mM to 0.09 mM;

(b) passing said sample through said capillary tube; and (c) separating said protein constituents and said lipoprotein constituents by electrophoresis.

* * * * *

UNITED STATES PATENT AND TRADEMARK OFFICE
CERTIFICATE OF CORRECTION

| | | |
|---|---|---|
| PATENT NO. | : 7,906,001 B2 | |
| APPLICATION NO. | : 11/125752 | |
| DATED | : March 15, 2011 | |
| INVENTOR(S) | : Frédéric Robert and Denis Simonin | |

It is certified that error appears in the above-identified patent and that said Letters Patent is hereby corrected as shown below:

Column 9, line 44 "$\beta_2$" should read --$\alpha_2$--.

Signed and Sealed this
Thirteenth Day of March, 2012

David J. Kappos
*Director of the United States Patent and Trademark Office*